United States Patent
Kini et al.

(10) Patent No.: US 11,952,350 B2
(45) Date of Patent: Apr. 9, 2024

(54) PROCESS FOR THE PREPARATION OF FUNGICIDALLY ACTIVE STROBILURIN COMPOUNDS AND INTERMEDIATES THEREOF

(71) Applicant: UPL LTD, Mumbai (IN)

(72) Inventors: Prashant Vasant Kini, Mumbai (IN); Santosh Ganpat Shelke, Mumbai (IN)

(73) Assignee: UPL LTD., Mumbai (IN)

( * ) Notice: Subject to any disclaimer, the term of this patent is extended or adjusted under 35 U.S.C. 154(b) by 136 days.

(21) Appl. No.: 17/603,430

(22) PCT Filed: Apr. 17, 2020

(86) PCT No.: PCT/IB2020/053656
§ 371 (c)(1),
(2) Date: Oct. 13, 2021

(87) PCT Pub. No.: WO2020/212928
PCT Pub. Date: Oct. 22, 2020

(65) Prior Publication Data
US 2022/0194903 A1    Jun. 23, 2022

(30) Foreign Application Priority Data
Apr. 18, 2019 (IN) .............................. 201921015651

(51) Int. Cl.
*C07D 239/52* (2006.01)
(52) U.S. Cl.
CPC .................. *C07D 239/52* (2013.01)
(58) Field of Classification Search
CPC ........................ C07D 239/52; C07D 413/12
See application file for complete search history.

(56) References Cited

U.S. PATENT DOCUMENTS

| 6,103,717 A | 8/2000 | Heinemann et al. |
| 2015/0011753 A1 | 1/2015 | Hindupur et al. |
| 2016/0200687 A1 | 7/2016 | Chen et al. |

FOREIGN PATENT DOCUMENTS

| CN | 102311392 A | 1/2012 |
| EP | 0382375 B1 | 3/1994 |
| EP | 2998299 A1 | 3/2016 |
| KR | 20140085204 A | 7/2014 |
| WO | 2008043978 A1 | 4/2008 |
| WO | 201490997 A1 | 12/2014 |
| WO | 2017060917 A1 | 4/2017 |

OTHER PUBLICATIONS

Heinemann, U. et al.; "Fluoxastrobin (HEC 5725)—the new dimension in strobilurin fungicides"; Pflanzenschutz-Nachrichten Bayer, vol. 57, Issue No. 3; 2004; pp. 299-318.
International Search Report and Written Opinion for International Application PCT/IB2020/053641; International Filing Date: Apr. 17, 2020; dated Jun. 19, 2020; 13 pages.
International Search Report and Written Opinion for International Application PCT/IB2020/053656; International Filing Date: Apr. 17, 2020; dated Jul. 14, 2020; 13 pages.
Liu, Y-G. et al.; "A Concise Synthesis of Azoxystrobin using a Suzuki Cross-Coupling Reaction"; Journal of Chemical Research, vol. 39; 2015; pp. 586-589.

*Primary Examiner* — Deepak R Rao
(74) *Attorney, Agent, or Firm* — CANTOR COLBURN LLP

(57) ABSTRACT

The present invention relates to a process for the preparation of strobilurin of compounds of Formula (I) of and its intermediates using 1,5,7-triazabicyclo[4.4.0]dec-5-ene or salts thereof, or derivatives thereof as a catalyst. The present invention provides the compounds of formula (I) in high yield and high purity.

19 Claims, No Drawings

PROCESS FOR THE PREPARATION OF FUNGICIDALLY ACTIVE STROBILURIN COMPOUNDS AND INTERMEDIATES THEREOF

CROSS REFERENCE TO RELATED APPLICATIONS

This application is a National Stage application of PCT/IB2020/053656, filed Apr. 17, 2020, which claims the benefit of priority to Indian Patent Application No. 201921015651, filed Apr. 18, 2019, both of which are incorporated by reference in their entirety herein.

FIELD OF INVENTION

The present invention relates to a process for the preparation of fungicidally active strobilurin compounds represented by Formula (I). The present invention also relates to process for the preparation of intermediates useful for making said strobilurin compounds.

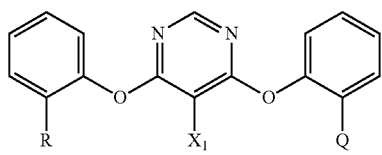
(I)

BACKGROUND OF THE INVENTION

Strobilurins are broad spectrum fungicides and are widely used pesticides both in foliar application and in seed treatment. Due to their wide spectrum activity profile, strobilurins are an important class of fungicides. Notable amongst this class of compounds are azoxystrobin, trifloxystrobin, fluoxastrobin, and picoxystrobin.

EP 382375 disclose various derivatives of propenoic acid useful as fungicides including azoxystrobin. This patent also discloses process for the preparation of azoxystrobin and intermediates thereof.

U.S. Pat. No. 6,103,717 discloses halogenopyrimidine compounds, process for their preparation, and their use as pesticides.

The conventional preparation of strobilurin fungicide compounds comprise multistep processes. Formation of impurities in the initial synthesis stages can lead to series of side reactions. Further it will require complex isolation procedures for the final product. Therefore, there is a need to develop an economic and commercially viable process for the preparation of strobilurin fungicides in good yield and high purity.

The present invention thus provides a process for the preparation of strobilurin compounds of Formula (I) and intermediates thereof using 1,5,7-triazabicyclo[4.4.0]dec-5-ene or salts thereof or its derivative compounds as a catalyst that provides desired compounds in high yield and substantially free from impurities.

OBJECT OF THE INVENTION

It is an object of the present invention to provide a process for the preparation of strobilurin compounds of Formula (I).

It is another object of the present invention to provide a process for the preparation of intermediate compounds useful for preparing the compound of formula (I).

It is another object of the present invention to provide the process for the preparation of strobilurin compounds of Formula (I) that is economical and environmentally friendly.

It is another object of the present invention to provide process for the preparation of intermediates useful for preparation of strobilurin compounds of Formula (I) that is simple and commercially viable.

It is another object of the present invention to provide process for the preparation of intermediates for the preparation of strobilurin compounds of Formula (I) in high yield and purity.

It is yet another object of the present invention to use 1,5,7-triazabicyclo[4.4.0]dec-5-ene or salts thereof or its derivative compounds as a catalyst for the preparation of strobilurin compounds of Formula (I) and intermediates thereof.

SUMMARY OF THE INVENTION

In an aspect the present invention provides a process for the preparation of strobilurin compounds of Formula (I) using 1,5,7-triazabicyclo[4.4.0]dec-5-ene, salts thereof, or derivatives thereof as a catalyst.

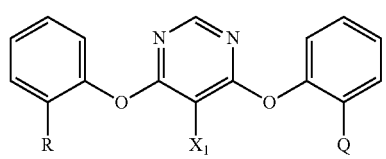
(I)

wherein R is selected from halogen and nitrile;
$X_1$ is selected from hydrogen and halogen;
Q is selected from methyl (E)-2-(3-methoxy) acrylate, methyl 2-(3,3-dimethoxy) propanoate, and 5,6-dihydro-1,4,2-dioxazin-3-yl-N-methoxymethanimine.

In another aspect, the present invention provides a process for the preparation of compounds of Formula (I) comprising:

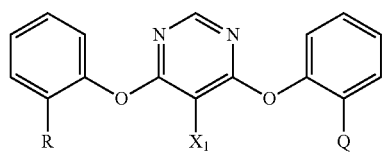
(I)

reacting compounds of Formula (II) with the compounds of Formula (III) in the presence of 1,5,7-triazabicyclo[4.4.0]dec-5-ene or salts thereof, or derivatives thereof as a catalyst;

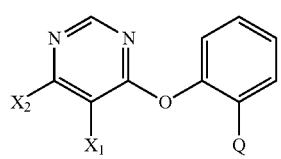
(II)

-continued

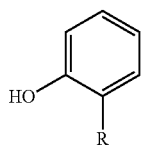
(III)

wherein,
R is selected from halogen and nitrile;
each of $X_1$ and $X_2$ is independently selected from hydrogen and halogen and Q is selected from methyl (E)-2-(3-methoxy) acrylate, methyl 2-(3,3-dimethoxy) propanoate, and 5,6-dihydro-1,4,2-dioxazin-3-yl-N-methoxymethanimine.

In another aspect the present invention provides a process for the preparation of intermediate compounds of Formula (II) comprising:

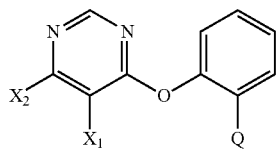
(II)

reacting compounds of Formula (V) with compounds of Formula (IV) in the presence of 1,5,7-triazabicyclo[4.4.0]dec-5-ene or salts thereof or derivatives thereof as a catalyst;

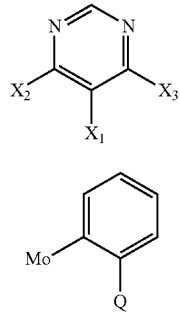
(V)

(IV)

wherein,
each of $X_1$, $X_2$ and $X_3$ is independently selected from hydrogen and halogen;
M is selected from hydrogen or an alkali metal;
Q is selected from methyl (E)-2-(3-methoxy) acrylate, methyl 2-(3,3-dimethoxy) propanoate, and 5,6-dihydro-1,4,2-dioxazin-3-yl-N-methoxymethanimine.

In another aspect the present invention provides a process for the preparation of compounds of Formula (I)

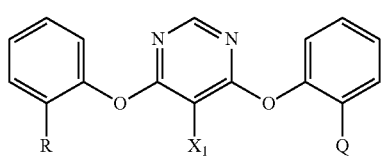
(I)

comprising:
reacting compounds of Formula (VI) with compounds of Formula (IV) in the presence of 1,5,7-triazabicyclo[4.4.0]dec-5-ene or salts thereof or derivatives thereof as a catalyst;

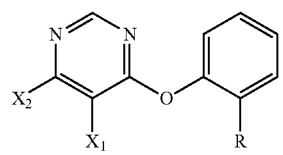
(VI)

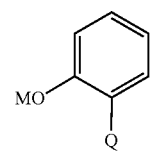
(IV)

wherein, R is selected from halogen and nitrile;
each $X_1$ and $X_2$ is independently selected from hydrogen and halogen;
M is selected from hydrogen or an alkali metal;
Q is selected from methyl (E)-2-(3-methoxy) acrylate, methyl 2-(3,3-dimethoxy) propanoate, and 5,6-dihydro-1,4,2-dioxazin-3-yl-N-methoxymethanimine.

In another aspect the present invention provides a process for the preparation of intermediate compounds of Formula (VI) comprising

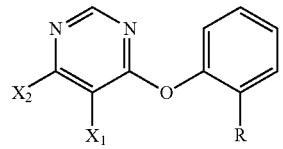
(VI)

reacting compound of Formula (V) with compound of Formula (III) in the presence of 1,5,7-triazabicyclo[4.4.0]dec-5-ene or salts thereof or derivatives thereof as a catalyst;

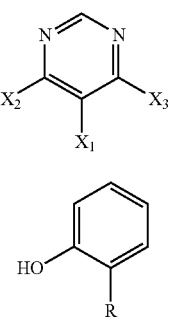
(V)

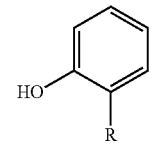
(III)

wherein, R is selected from halogen and nitrile; each of $X_1$, $X_2$ and $X_3$ is independently selected from hydrogen and halogen.

In another aspect the present invention provides a process for the preparation of compound of Formula (I) comprising:

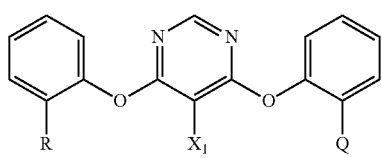
(I)

(i) reacting compound of Formula (V) with compound of Formula (IV) in the presence of 1,5,7-triazabicyclo[4.4.0]dec-5-ene or salts thereof or derivatives thereof as a catalyst to obtain compound of Formula (II)

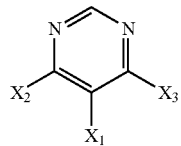
(V)

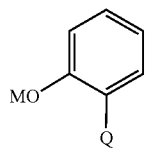
(IV)

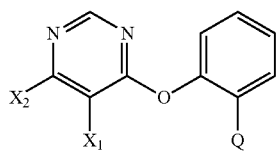
(II)

(ii) reacting compound of Formula (II) with compound of Formula (III) in the presence of 1,5,7-triazabicyclo[4.4.0]dec-5-ene or salts thereof or derivatives thereof as a catalyst to obtain compound of Formula (I).

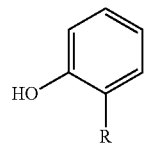
(III)

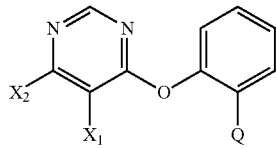
(II)

wherein, R, $X_1$, $X_2$, $X_3$, M and Q have same meaning as defined above.

In yet another aspect the present invention provides a process for the preparation of compound of Formula (I)

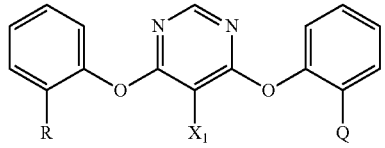
(I)

comprising:
(i) reacting compound of Formula (V) with compound of Formula (III) in the presence of 1,5,7-triazabicyclo[4.4.0]dec-5-ene, salts thereof, or derivatives thereof as a catalyst to obtain compound of Formula (VI)

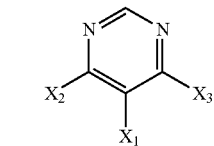
(V)

(III)

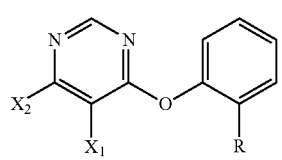
(VI)

(ii) reacting compound of (VI) with compound of Formula (IV) in the presence of 1,5,7-triazabicyclo[4.4.0]dec-5-ene or salts thereof, or derivatives thereof as a catalyst to obtain compound of Formula (I);

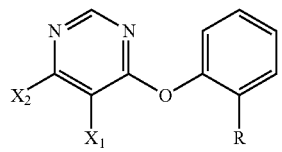
(VI)

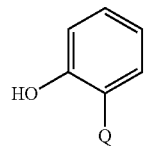
(IV)

wherein, R is selected from halogen or nitrile, $X_1$, $X_2$, $X_3$, and Q has same meaning as above.

In another aspect the present invention provides a process for the preparation of azoxystrobin and its intermediates using 1,5,7-triazabicyclo[4.4.0]dec-5-ene or salts thereof, or derivatives thereof as a catalyst.

In another aspect the present invention provides a process for the preparation of fluoxastrobin and its intermediates using 1,5,7-triazabicyclo[4.4.0]dec-5-ene or salts or derivatives thereof as a catalyst.

In another aspect the process of the present invention provides a strobilurin compound of Formula (I) in high yield and substantially free of impurities.

In another aspect strobilurin compounds of Formula (I) prepared according to the present process have purity greater than 95% preferably greater than 98%.

The processes according to the present invention provide highly pure strobilurin compounds of Formula (I) that are substantially free of impurities; and in particular a dimer impurity below 0.15% by weight.

The processes according to the present process provide intermediates of Formula (II) and Formula (VI) for strobilurin compounds that are substantially free of impurities, in particular, a dimer impurity below 0.15% by weight.

DETAILED DESCRIPTION OF THE INVENTION

For the purposes of the following detailed description, it is to be understood that the invention may assume various alternative variations and step sequences, except where expressly specified to the contrary. Moreover, other than in any operating examples, or where otherwise indicated, all numbers expressing, for example, quantities of materials/ingredients used in the specification are to be understood as being modified in all instances by the term "about". The term "about" shall be interpreted to mean "approximately" or "reasonably close to" and any statistically insignificant variations therefrom.

Thus, before describing the present invention in detail, it is to be understood that this invention is not limited to particularly exemplified systems or process parameters that may of course, vary. It is also to be understood that the terminology used herein is for the purpose of describing particular embodiments of the invention only and is not intended to limit the scope of the invention in any manner. The use of examples anywhere in this specification including examples of any terms discussed herein is illustrative only, and in no way limits the scope and meaning of the invention or of any exemplified term. Likewise, the invention is not limited to various embodiments given in this specification.

It must be noted that, as used in this specification, the singular forms "a," "an" and "the" include plural referents unless the content clearly dictates otherwise. The terms "preferred" and "preferably" refer to embodiments of the invention that may afford certain benefits, under certain circumstances.

As used herein, the terms "comprising" "including," "having," "containing," "involving," and the like are to be understood to be open-ended, i.e., to mean including but not limited to.

As used herein halogen includes chlorine, bromine, iodine, and fluorine.

As used herein, alkali metal includes lithium, sodium, potassium, etc.

The present invention provides an efficient and economical process for the preparation of the compound of Formula (I) in good yield and high purity. The catalyst used in the present process facilitates complete conversion of reactants to the desired product and simultaneously reducing the formation of undesired by products/impurity.

The inventors of the present invention have surprisingly found that the strobilurin compounds of Formula (I) that are substantially free of certain impurities can be prepared in excellent yield using 1,5,7-triazabicyclo[4.4.0]dec-5-ene (TABD) or salts thereof, or derivatives thereof as catalyst.

Hereunder described are the embodiments of the present invention in detail.

According to the present invention, there is provided a process for the preparation of strobilurin compounds of Formula (I) and intermediate compounds useful for preparation of compounds of formula (I) that is commercially viable and effective for large scale production.

Accordingly, there is provided a process for the preparation of intermediates of compounds of Formula (II) and (VI) for making strobilurin compounds of Formula (I) wherein the process is carried out using 1,5,7-triazabicyclo[4.4.0]dec-5-ene or salts thereof, or derivatives thereof as catalyst.

In an aspect the present invention provides a process for the preparation of strobilurin compounds of Formula (I) using 1,5,7-triazabicyclo[4.4.0]dec-5-ene or salts thereof, or derivatives thereof as a catalyst.

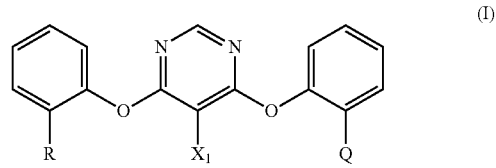

(I)

wherein R is selected from halogen and nitrile;
$X_1$ is selected from hydrogen and halogen; halogen is chlorine, bromine, iodine or fluorine.
Q is selected from methyl (E)-2-(3-methoxy) acrylate, methyl 2-(3,3-dimethoxy) propanoate, and 5,6-dihydro-1,4,2-dioxazin-3-yl-N-methoxymethanimine.

According to the present invention 1,5,7-triazabicyclo[4.4.0]dec-5-ene includes salts thereof, and derivative compounds thereof. Preferably 1,5,7-triazabicyclo[4.4.0]dec-5-ene includes compounds represented by the Formula (VII), formula (VIIa), formula (VIIb) and formula (VIIc).

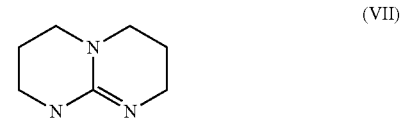

(VII)

(VIIa)

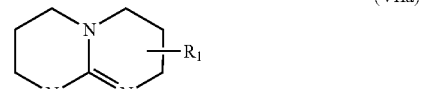

(VIIb)

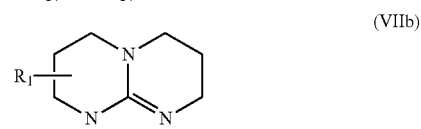

(VIIc)

wherein,
$R_1$ is selected from the group consisting of hydrogen, hydroxyl, $C_1$-$C_{20}$ hydrocarbonyl, amino, $C_1$-$C_6$ alkyl amino, cyano or halogen;
wherein,
$C_1$-$C_{20}$ hydrocarbonyl is unsubstituted or substituted, wherein the substituent is independently selected from the group consisting of straight chain hydrocarbonyl, cyclic hydrocarbonyl, saturated hydrocarbonyl and unsaturated hydrocarbonyl. The saturated hydrocarbonyl can be, for example, any of methyl, ethyl, propyl, isopropyl, n-butyl, isobutyl, tert-butyl, amyl, and hexyl, and the unsaturated hydrocarbonyl can be, for example, any of propenyl, isopropenyl, butenyl, isobutenyl, pentenyl, and hexenyl;

$C_1$-$C_6$ alkyl amino is unsubstituted or mono or di substituted, for example, methylamino, dimethyl amino, diethyl amino, diisopropyl and halogen is chlorine, bromine, iodine or fluorine.

In an aspect, 1,5,7-triazabicyclo[4.4.0]dec-5-ene includes its salts.

Salts of 1,5,7-triazabicyclo[4.4.0]dec-5-ene include inorganic salts and organic salts. Inorganic salts include hydrochloride, sulphate, nitrate and phosphate. Organic salts include formate, acetate, benzoate, trifluoroacetate, citrate, succinate, maleate, fumarate and oxalate.

In an embodiment the catalyst 1,5,7-triazabicyclo[4.4.0]dec-5-ene, or its salts thereof, or derivative compounds thereof is used in an amount from about 0.01 mol % to about 50 mol %.

In an embodiment the catalyst 1,5,7-triazabicyclo[4.4.0]dec-5-ene, or its salts thereof or derivatives thereof is used in an amount from about 0.01 mol % to about 20 mol %.

In a preferred embodiment the catalyst 1,5,7-triazabicyclo[4.4.0]dec-5-ene, or its salts thereof or derivatives thereof is used in an amount from about 0.1 mol % to about 5 mol %.

In another aspect, the process for the preparation of compounds of Formula (I) comprising:

(I)

reacting compounds of Formula (II) with the compounds of Formula (III) in the presence of 1,5,7-triazabicyclo[4.4.0]dec-5-ene or salts thereof, or derivatives thereof as a catalyst;

(II)

(III)

wherein,

R is selected from halogen and nitrile;

each of $X_1$ and $X_2$ is independently selected from hydrogen and halogen; and Q is selected from methyl (E)-2-(3-methoxy) acrylate, methyl 2-(3,3-dimethoxy) propanoate, and 5,6-dihydro-1,4,2-dioxazin-3-yl-N-methoxymethanimine.

In an embodiment the process is carried out at a temperature in the range of about 0-150° C.

In an embodiment the process is carried out at a temperature in the range of about 30-120° C.

In preferred embodiment the process is carried out at a temperature in the range of about 50-120° C.

In an embodiment the process is carried out at a temperature in the range of about 50-100° C.

In an embodiment the process is carried out at a temperature in the range of about 50-70° C.

In an embodiment the process is carried out for a period of about 2 to 10 hrs.

In an embodiment the process is carried out for a period of about 5 to 8 hrs.

In another aspect the present invention provides a process for the preparation of intermediate compounds of Formula (II) comprising:

(II)

reacting compounds of Formula (V) with compounds of Formula (IV) in the presence of 1,5,7-triazabicyclo[4.4.0]dec-5-ene or salts thereof, or derivatives thereof as a catalyst;

(V)

(IV)

wherein, each of $X_1$, $X_2$ and $X_3$ is independently selected from hydrogen and halogen;

M is selected from hydrogen or an alkali metal;

Q is selected from methyl (E)-2-(3-methoxy) acrylate, methyl 2-(3,3-dimethoxy) propanoate, and 5,6-dihydro-1,4,2-dioxazin-3-yl-N-methoxymethanimine.

In an embodiment the process is carried out at a temperature in the range of about 0-150° C.

In an embodiment the process is carried out at a temperature in the range of about 30-120° C.

In preferred embodiment the process is carried out at a temperature in the range of about 50-120° C.

In an embodiment the process is carried out at a temperature in the range of about 50-100° C.

In an embodiment the process is carried out at a temperature in the range of about 50-70° C.

In an embodiment the process is carried out for a period of about 4 to 20 hrs.

In an embodiment the process is carried out for a period of about 5 to 10 hrs.

In an embodiment the process is carried out for a period of about 5 to 8 hrs.

In another aspect the present invention provides a process for the preparation of compound of Formula (I) comprising:

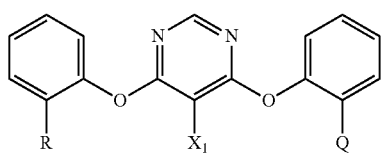
(I)

(i) reacting compound of Formula (V) with compound of Formula (IV) in the presence of 1,5,7-triazabicyclo[4.4.0]dec-5-ene or salts or derivatives thereof as a catalyst to obtain compounds of Formula (II)

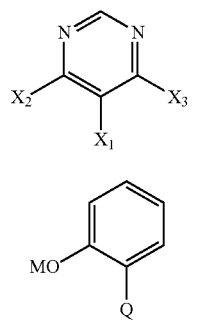

(V)

(IV)

(II)

(ii) reacting compound of Formula (II) with compound of Formula (III) in the presence of 1,5,7-triazabicyclo[4.4.0]dec-5-ene or salts or derivatives thereof as a catalyst to obtain compound of Formula (I);

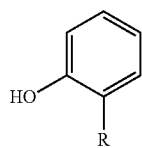
(III)

(iii) optionally isolating the compound of Formula (I), wherein, R, $X_1$, $X_2$, $X_3$, M and Q has same meaning as defined above.

In an embodiment the process is carried out at a temperature in the range of about 0-150° C.

In an embodiment the process is carried out at a temperature in the range of about 30-120° C.

In preferred embodiment the process is carried out at a temperature in the range of about 50-120° C.

In an embodiment the process is carried out at a temperature in the range of about 50-100° C.

In an embodiment the process is carried out at a temperature in the range of about 50-70° C.

In an embodiment the process is carried out for a period of about 2 to 30 hrs.

In an embodiment the process is carried out for a period of about 2 to 20 hrs

In an embodiment the process is carried out for a period of about 5 to 10 hrs.

In an embodiment the process is carried out for a period of about 5 to 8 hrs.

In an embodiment, the compounds of Formula (IV) are prepared from compound of Formula (VIII) wherein A is selected from carbonyl and hetero substituted alkene and B is selected from carbonyl and alkene.

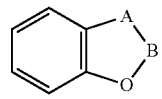
(VIII)

In another aspect the present invention provides a process for the preparation of compound of Formula (I) comprising:

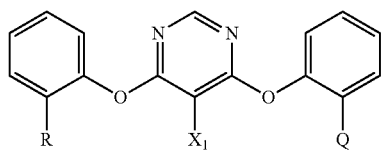
(I)

reacting compound of (VI) with compound of Formula (IV) in the presence of 1,5,7-triazabicyclo[4.4.0]dec-5-ene or salts thereof, or derivatives thereof as a catalyst to obtain compound of Formula (I);

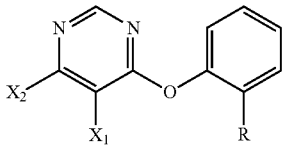
(VI)

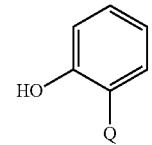
(IV)

wherein, R is selected from halogen or nitrile, $X_1$, $X_2$, $X_3$, and Q has same meaning as above.

In an embodiment the process is carried out at a temperature in the range of about 0-150° C.

In an embodiment the process is carried out at a temperature in the range of about 30-120° C.

In preferred embodiment the process is carried out at a temperature in the range of about 50-120° C.

In an embodiment the process is carried out at a temperature in the range of about 50-100° C.

In an embodiment the process is carried out at a temperature in the range of about 50-70° C.

In an embodiment the process is carried out for a period of about 1 to 12 hrs.

In an embodiment the process is carried out for a period of about 5 to 10 hrs.

In another aspect the present invention provides a process for the preparation of intermediate compounds of Formula (VI) comprising

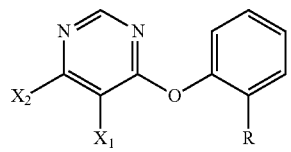
(VI)

reacting compound of Formula (V) with compound of Formula (III) in the presence of 1,5,7-triazabicyclo[4.4.0]dec-5-ene or salts or derivatives thereof as a catalyst;

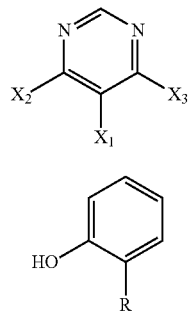
(V)

(III)

wherein, R is selected from halogen and nitrile;
each of $X_1$, $X_2$ and $X_3$ is independently selected from hydrogen and halogen.

In an embodiment the process is carried out at a temperature in the range of about 0-150° C.

In an embodiment the process is carried out at a temperature in the range of about 30-120° C.

In preferred embodiment the process is carried out at a temperature in the range of about 50-120° C.

In an embodiment the process is carried out at a temperature in the range of about 50-100° C.

In an embodiment the process is carried out at a temperature in the range of about 50-70° C.

In an embodiment the process is carried out for a period of about 1 to 12 hrs.

In an embodiment the process is carried out for a period of about 5 to 10 hrs.

In yet another aspect the present invention provides a process for the preparation of compound of Formula (I)

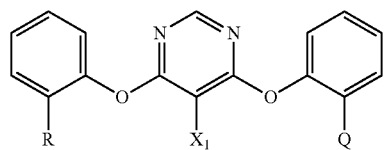
(I)

comprising:
(i) reacting compound of Formula (V) with compound of Formula (III) in the presence of 1,5,7-triazabicyclo[4.4.0]dec-5-ene, salts thereof, or derivatives thereof as a catalyst to obtain compound of Formula (VI)

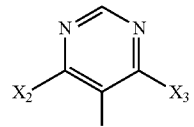
(V)

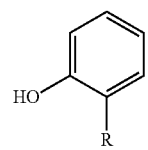
(III)

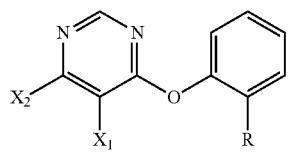
(VI)

(ii) reacting compound of (VI) with compound of Formula (IV) in the presence of 1,5,7-triazabicyclo[4.4.0]dec-5-ene or salts thereof, or derivatives thereof as a catalyst to obtain compound of Formula (I);

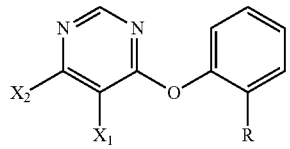
(VI)

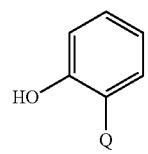
(IV)

(iv) optionally isolating the compound of Formula (I);
wherein, R is selected from halogen or nitrile, $X_1$, $X_2$, $X_3$, and Q has same meaning as above.

In an embodiment the process is carried out at a temperature in the range of about 0-150° C.

In an embodiment the process is carried out at a temperature in the range of about 30-120° C.

In preferred embodiment the process is carried out at a temperature in the range of about 50-120° C.

In an embodiment the process is carried out at a temperature in the range of about 50-100° C.

In an embodiment the process is carried out at a temperature in the range of about 50-70° C.

In an embodiment the process is carried out for a period of about 3 to 24 hrs.

In an embodiment the process is carried out for a period of about 5 to 10 hrs.

In an embodiment, the compound of Formula (I) encompasses azoxystrobin.

In another aspect the present invention provides a process for the preparation of azoxystrobin and its intermediates using 1,5,7-triazabicyclo[4.4.0]dec-5-ene or salts thereof, or derivatives thereof as a catalyst.

In an embodiment, the present invention provides a process for the preparation of strobilurin compound of Formula (I) wherein $X_1$ is hydrogen, R is —CN and Q is methyl (E)-2-(3-methoxy)acrylate group as represented by Formula (Ia). The compound of Formula (Ia) is referred to as azoxystrobin.

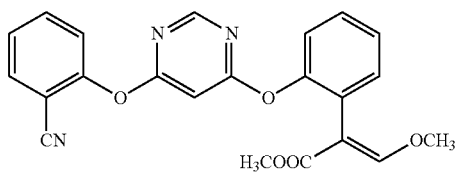

(Ia)

In an embodiment, the present invention provides a process for the preparation of the compound of Formula (Ia) and intermediates thereof.

Accordingly, the entire process is technically advanced over the conventional process, an efficient and feasible process for preparation strobilurin compounds for example azoxystrobin, fluoxasrobin and the like and intermediates thereof providing the products in high yield and high purity In an embodiment, the compound of Formula (I) encompasses fluoxastrobin. In an embodiment, the present invention provides a process for the preparation of a compound of Formula (I) wherein $X_1$ is fluorine and R is chlorine and Q is (E)-5,6-dihydro-1,4,2-dioxazin-3-yl-N-methoxymethanimine group as represented by Formula (Ib). Compound of Formula (Ib) is referred to as fluoxastrobin.

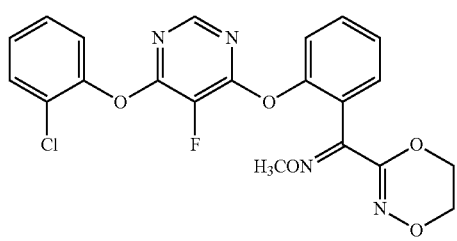

(Ib)

In another embodiment, the present invention provides a process for the preparation of the compound of Formula (Ib) and intermediates thereof.

In an embodiment the present invention provides key intermediate compound of Formula (II) useful for the preparation of compound of Formula (Ia) and (Ib).

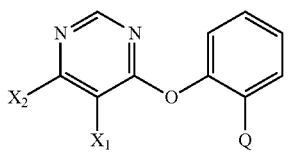

(II)

Accordingly there is provided a compound of Formula (Ia) prepared by a process which proceeds via the intermediate compounds of Formula (II) prepared in the presence of 1,5,7-triazabicyclo[4.4.0]dec-5-ene or salts thereof, or derivatives thereof as a catalyst.

Accordingly there is provided a compound of Formula (Ib) prepared by a process which proceeds via the intermediate compounds of Formula (II) prepared in the presence of 1,5,7-triazabicyclo[4.4.0]dec-5-ene or salts thereof, or derivatives thereof as a catalyst.

In an embodiment, the key intermediate of compound of Formula (II) wherein $X_1$ is hydrogen, $X_2$ is chlorine and Q is methyl (E)-2-(3-methoxy)acrylate group as represented by Formula (IIa), is used for preparing the compound of formula (Ia).

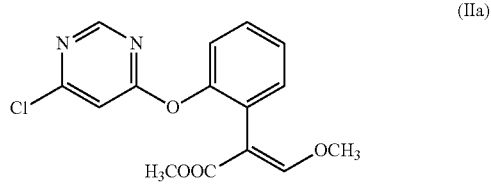

(IIa)

In yet another embodiment, the process for the preparation of compound of Formula (Ia) proceeds via the compound of Formula (IIa) in presence of 1,5,7-triazabicyclo[4.4.0]dec-5-ene or salts thereof, or derivatives thereof as a catalyst.

In another embodiment, the key intermediate of compound of Formula (II) wherein $X_1$ is hydrogen, $X_2$ is chlorine and Q is methyl 2-(3,3-dimethoxy)propanoate group as represented by Formula (IIb), is used for preparing the compound of formula (Ia).

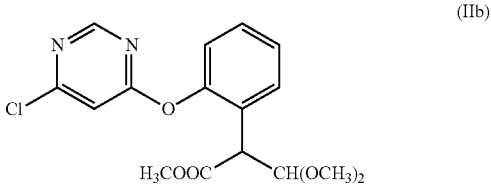

(IIb)

In yet another embodiment, the process for the preparation of compound of Formula (Ia) proceeds via the compound of Formula (IIb) in presence of 1,5,7-triazabicyclo[4.4.0]dec-5-ene or salts thereof, or derivatives thereof as a catalyst.

In yet another embodiment, the process for the preparation of compound of Formula (Ia) proceeds via a mixture of compounds of Formula (IIa) and Formula (IIb).

With respect to the present invention compound of Formula (IIb) can be converted to compound of Formula (IIa) by known methods.

In an embodiment, the key intermediate of compound of Formula (II) wherein $X_1$ is fluorine, $X_2$ is chlorine and Q is (E)-5,6-dihydro-1,4,2-dioxazin-3-yl-N-methoxymethanimine as represented by Formula (IIc), is used for preparing the compound of formula (Ib).

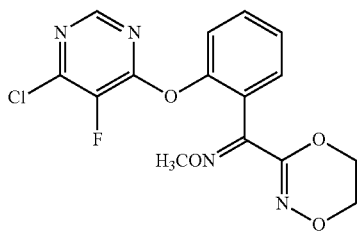
(IIc)

In yet another embodiment, the process for the preparation of compound of Formula (Ib) proceeds via the compound of Formula (IIc) in presence of 1,5,7-triazabicyclo[4.4.0]dec-5-ene or salts thereof, or derivatives thereof as a catalyst.

In an embodiment the process for preparation of compound of formula (I) involves a compound of Formula (III) wherein R is —CN, represented by Formula (IIIa).

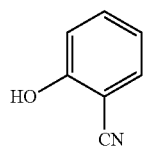
(IIIa)

In another embodiment the process for preparation of compound of Formula (Ia) comprises reaction of compounds of Formula (IIa) with a compound of Formula (IIIa) in the presence of 1,5,7-triazabicyclo[4.4.0]dec-5-ene or salts thereof, or derivatives thereof as a catalyst.

In an embodiment the process for preparation of compound of formula (I) involves a compound of Formula (III) wherein when R is chlorine is represented by Formula (IIIb).

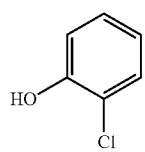
(IIIb)

In another embodiment the process for preparation of compound of Formula (Ib) comprises reaction of compounds of Formula (IIc) with a compound of Formula (IIIb) in the presence of 1,5,7-triazabicyclo[4.4.0]dec-5-ene or salts thereof, or derivatives thereof as a catalyst.

In an embodiment, the present process involves a compound of Formula (IV) wherein Q is methyl (E)-2-(3-methoxy)acrylate group and M is sodium, as represented by Formula (IVa).

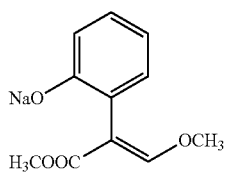
(IVa)

In another embodiment, the compound of Formula (IV) wherein Q is methyl 2-(3,3-dimethoxy)propanoate group and M is sodium is represented by Formula (IVb).

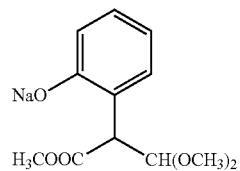
(IVb)

In yet another embodiment, the process according to the invention is carried out using a mixture of compounds of Formula (IVa) and Formula (IVb).

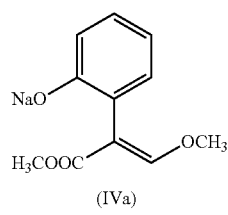 + 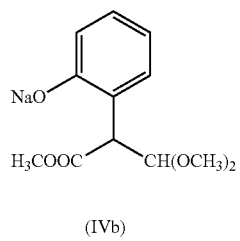

(IVa)                    (IVb)

In an embodiment the compounds of Formula (IV) is prepared from compound of Formula (VIII) in situ reaction.

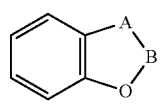
(VIII)

Typically, the compound of formula (VIII) wherein A is selected from carbonyl and hetero substituted alkene and B is selected from carbonyl and alkene, referred as compounds of Formula (VIIIa).

Preferably the compound of Formula (IVa) and compound of Formula (IVb) can be prepared from 3-(methoxy methylene)-2(3H)-benzofuranone of Formula (VIIIa) in situ.

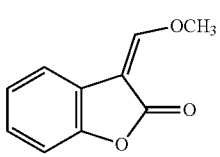
(VIIIa)

In another embodiment the compound of Formula (IV) used in the process, wherein Q is (E)-5,6-dihydro-1,4,2-dioxazin-3-yl-N-methoxymethanimine group and M is hydrogen as represented by Formula (IVc)

(IVc)

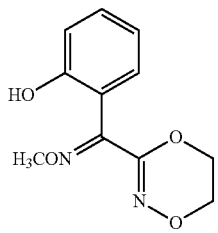

Typically, the compound of Formula (IVc) is prepared from compound of Formula (VIIIb) by processes known in the literature for example EP688769.

(VIIIb)

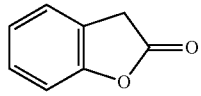

In an embodiment, the compound of Formula (V) wherein $X_1$ is hydrogen, $X_2$ and $X_3$ are chlorine is represented by Formula (Va).

(Va)

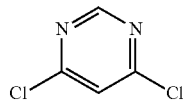

In another embodiment, the compound of Formula (V) wherein $X_1$ is fluorine and $X_2$ and $X_3$ are chlorine is represented by Formula (Vb).

(Vb)

In an embodiment, the process for preparation of a compound of Formula (Ia) comprises
 (a) reacting a compound of formula (IVa) with a compound of formula (Va) in presence of 1,5,7-triazabicyclo[4.4.0]dec-5-ene or salts thereof, or derivatives thereof as a catalyst to get compound of formula (IIa) and (IVa)

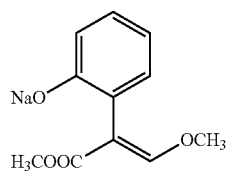

(Va)

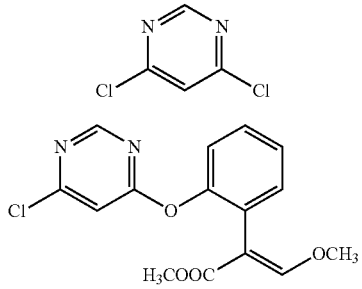

(IIa)

(b) converting compound of formula (IIa) to a compound of formula (Ia).

(Ia)

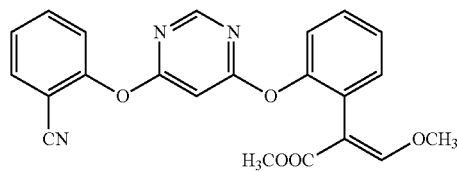

The process of converting compound of formula (IIa) to a compound of formula (Ia) comprises reacting the compound of formula (IIa) with compound of formula (IIIa) in presence of 1,5,7-triazabicyclo[4.4.0]dec-5-ene or salts thereof, or derivatives thereof as a catalyst.

(IIIa)

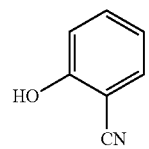

(IIa)

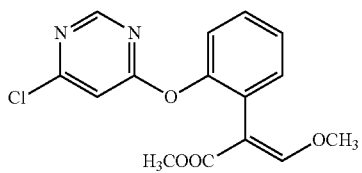

Typically, the process for preparation of compound of formula (Ia) comprises two steps,
 1) process for preparing the compound of formula (IIa) and
 2) converting the compound of formula (IIa) to compound of formula (Ia).
In one preferred embodiment the process for preparation of compound of formula (Ia) comprises
 1) reaction of 4,6-dichloropyrimidine with 3-(methoxy methylene)-2(3H)-benzofuranone in presence of a catalytic amount of 1,5,7-triazabicyclo[4.4.0]dec-5-ene and suitable base;
 2) optionally isolating the product from the reaction mixture;
 3) optionally purifying the compound by crystallization using suitable solvent to obtain pure methyl (2E)-2-{2-[(6-chloropyrimidin-4-yl)oxy]phenyl}-3-methoxyacrylate (IIa) and 4) converting pure methyl (2E)-2-{2-[(6-chloropyrimidin-4-yl)oxy]phenyl}-3-methoxyacrylate (IIa) to compound of formula (Ia).

The compound, methyl (2E)-2-{2-[(6-chloropyrimidin-4-yl)oxy]phenyl}-3-methoxyacrylate (IIa) produced according to the present invention is having high purity of about 97.5%, and reduced dimer content i.e. below 1%. The compound of formula (IIa) thus obtained is used for preparing the compound of formula (Ia). Typically, the process for preparation of compound of formula (IIa) comprises reaction of 4,6-dichloropyrimidine with 3-(methoxy methylene)-2(3H)-benzofuranone in presence of 1,5,7-triazabicyclo[4.4.0]dec-5-ene. The reaction is carried out in a solvent for example methyl formate and a suitable base for example sodium methoxide.

The reaction mass is stirred at temperature of about 50-80° C.

The product thus obtained is (IIb) or mixture of (IIa) and (IIb), and it is converted to compound of formula (IIa) i.e. methyl (2E)-2-{2-[(6-chloropyrimidin-4-yl)oxy]phenyl}-3-methoxyacrylate (IIa).

The compound of formula (IIa) with high purity of about 97 to 99%, and reduced dimer content i.e. below 1% is used for preparing the compound of formula (Ia).

In another preferred embodiment, the process for preparation of azoxystrobin (Ia) comprises reaction of methyl (2E)-2-{2-[6-chloropyrimidin-4-yloxy]phenyl}-3-methoxyacrylate (IIa) with 2-cyanophenol in presence of catalytic amount of 1,5,7-triazabicyclo[4.4.0]dec-5-ene, in presence of suitable base for example potassium carbonate and solvent for example dimethylformamide (DMF). The reaction is carried out at temperature of about 50 to 100° C. Optionally the compound thus obtained is crystalized from a solvent selected from alcohol for example methanol and water to obtain azoxystrobin.

Azoxystrobin prepared according to the present invention is having high purity of at least 98.9% and reduced dimer impurity content preferably 0.5% more preferably 0.2%.

In another embodiment, the process for preparation of a compound of Formula (Ia) comprises
(a) reacting a compound of formula (IVb) with a compound of formula (Va) in presence of 1,5,7-triazabicyclo[4.4.0]dec-5-ene or salts thereof, or derivatives thereof as a catalyst to get compound of formula (IIb) and

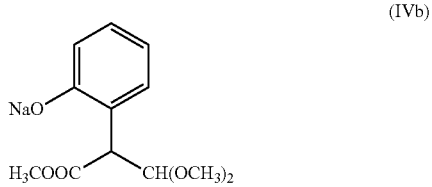

(IVb)

(Va)

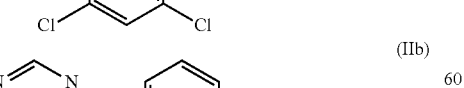

(IIb)

(b) converting compound of formula (IIb) to a compound of formula (Ia).

Typically, the compound of formula (IIb) is insitu converted to a compounds of Formula (IIa) for producing a compound of formula (Ia).

The process of converting compound of formula (IIb) to a compound of formula (Ia) comprises reacting the compound of formula (IIa) with compound of formula (IIIb) in presence of 1,5,7-triazabicyclo[4.4.0]dec-5-ene or salts thereof, or derivatives thereof as a catalyst.

In yet another embodiment, the process according to the present invention provides a mixture of compounds of Formula (IIa) and Formula (IIb).

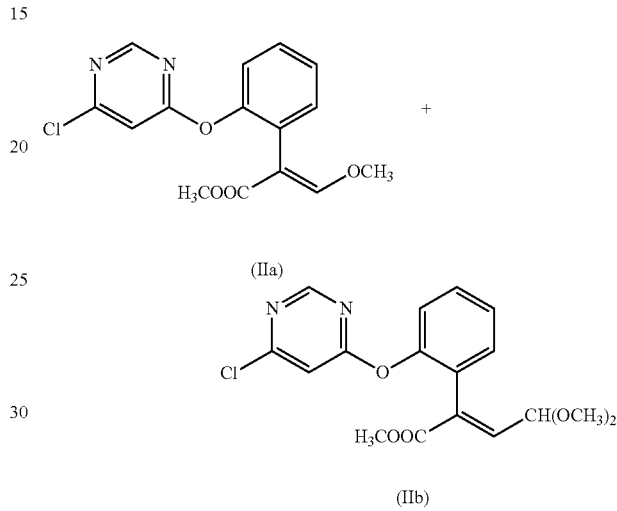

With respect to the present invention the compound of Formula (IIb) can be converted to compound of Formula (IIa) by known methods.

In another embodiment there is provided a process for preparation of a compound of Formula (Ib).

Typically, the process for preparation of compound of formula (Ib) comprises two steps,
1) process for preparing the compound of formula (IIc) and
2) converting the compound of formula (IIc) to compound of formula (Ib).

In one preferred embodiment the process for preparation of compound of formula (Ib) comprises
1) reaction of 4,6-Dichloro-5-fluoropyrimidine with (E)-5,6-dihydro-1,4,2-dioxazin-3-yl-(2-hydroxyphenyl) methanone-O-methyloxime in presence of catalytic amount of 1,5,7-triazabicyclo[4.4.0]dec-5-ene and suitable base;
2) optionally isolating the product from the reaction mixture;
3) optionally purifying the compound by crystallization using suitable solvent to obtain pure Methanone, [2-[(6-chloro-5-fluoro-4-pyrimidinyl)oxy]phenyl](5,6-dihydro-1,4,2-dioxazin-3-yl)-, O-methyloxime, (E);
4) converting Methanone, [2-[(6-chloro-5-fluoro-4-pyrimidinyl)oxy]phenyl](5,6-dihydro-1,4,2-dioxazin-3-yl)-, O-methyloxime, (E) (IIc) to compound of formula (Ib).

The compound, Methanone, [2-[(6-chloro-5-fluoro-4-pyrimidinyl)oxy]phenyl](5,6-dihydro-1,4,2-dioxazin-3-yl)-, O-methyloxime, (E) (IIc) produced according to the present invention is having high purity of about 97 to 99% and reduced dimer content i.e. below 1%. The compound of formula (IIc) thus obtained is used for preparing the compound of formula (Ib).

The process of converting compound of formula (IIc) to a compound of formula (Ib) comprises reacting the compound of formula (IIc) with compound of formula (IIIb) in presence of 1,5,7-triazabicyclo[4.4.0]dec-5-ene or salts thereof or derivatives thereof as a catalyst.

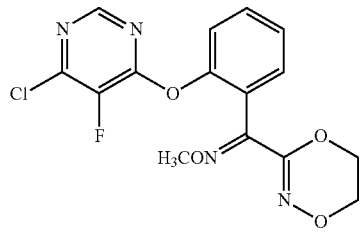

(IIc)

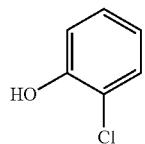

(IIIb)

Alternatively, the compound of formula (I) is prepared from the intermediate compound of formula (VI).

In another aspect the present invention provides a process for the preparation of compounds of Formula (I) comprising

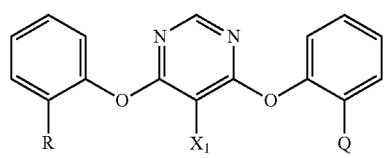

(I)

reacting compounds of Formula (VI) with compounds of Formula (IV) in the presence of 1,5,7-triazabicyclo[4.4.0]dec-5-ene or salts thereof, or derivatives thereof as a catalyst;

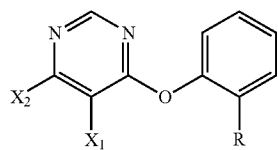

(VI)

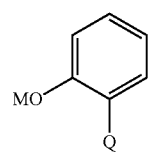

(IV)

wherein, R is selected from halogen and nitrile;
each of $X_1$ and $X_2$ is independently selected from hydrogen and halogen;
M is selected from hydrogen or an alkali metal;
Q is selected from methyl (E)-2-(3-methoxy) acrylate, methyl 2-(3,3-dimethoxy) propanoate, and 5,6-dihydro-1,4,2-dioxazin-3-yl-N-methoxymethanimine.

In an embodiment the process according to the present invention is carried out using a compound of Formula (VI) wherein R is —CN, $X_1$ is hydrogen and $X_2$ is chlorine as represented by Formula (VIa).

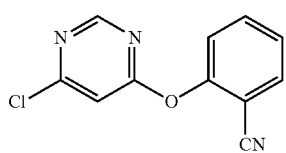

(VIa)

In an embodiment the process according to the present invention is carried out using a compound of Formula (VI) wherein R is chlorine, $X_1$ is fluorine and $X_2$ is chlorine as represented by Formula (VIb).

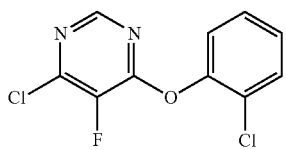

(VIb)

The compound of Formula (Ia) is prepared using the compound of Formula (VIa) and (IVa)/(IVb) or the mixture of these two compounds in presence of 1,5,7-triazabicyclo[4.4.0]dec-5-ene or salts thereof, or derivatives thereof as a catalyst.

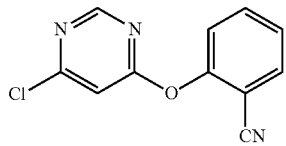

(VIa)

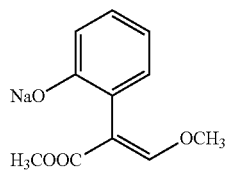

(IVa)

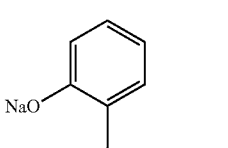

(IVb)

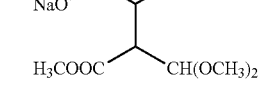

Accordingly there is also provided a compound of Formula (Ib) prepared by a process which proceeds via the intermediate compounds of Formula (VIb) prepared in the presence of 1,5,7-triazabicyclo[4.4.0]dec-5-ene or salts thereof, or derivatives thereof as a catalyst.

In an embodiment, the compounds of Formula (IV) are prepared from compound of Formula (VIII) wherein A is selected from carbonyl and hetero substituted alkene and B is selected from carbonyl and alkene.

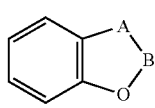
(VIII)

In another aspect the present invention provides a process for the preparation of intermediate compounds of Formula (VI) comprising

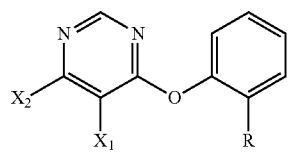
(VI)

reacting compound of Formula (V) with compound of Formula (III) in the presence of 1,5,7-triazabicyclo[4.4.0]dec-5-ene or salts thereof, or derivatives thereof as a catalyst;

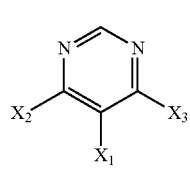
(V)

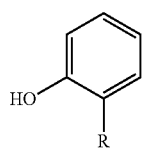
(III)

wherein, R is selected from halogen and nitrile;

each of $X_1$, $X_2$ and $X_3$ is independently selected from hydrogen and halogen;

In yet another aspect the present invention provides a process for the preparation of compound of Formula (I)

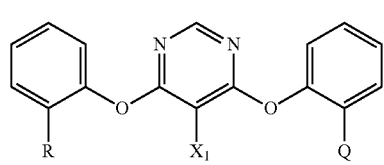
(I)

comprising:

(iii) reacting compound of Formula (V) with compound of Formula (III) in the presence of 1,5,7-triazabicyclo[4.4.0]dec-5-ene, salts thereof, or derivatives thereof as a catalyst to obtain compound of Formula (VI)

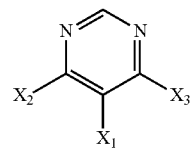
(V)

(III)

(VI)

(iv) reacting compound of (VI) with compound of Formula (IV) in the presence of 1,5,7-triazabicyclo[4.4.0]dec-5-ene or salts thereof, or derivatives thereof as a catalyst to obtain compound of Formula (I);

(VI)

(IV)

wherein, R is selected from halogen or nitrile, $X_1$, $X_2$, $X_3$, and Q has same meaning as above.

In an embodiment, the process for preparation of a compound of Formula (Ia) comprises (a) reacting a compound of formula (Va) with a compound of formula (IIIa) in presence of 1,5,7-triazabicyclo[4.4.0]dec-5-ene or salts thereof, or derivatives thereof as a catalyst to get compound of formula (VIa) and

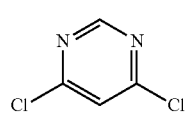
(Va)

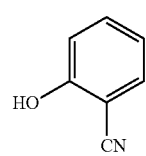
(IIIa)

-continued

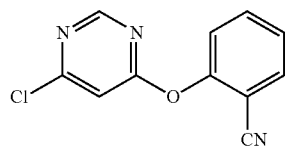
(VIa)

(b) converting compound of formula (VIa) to a compound of formula (Ia).

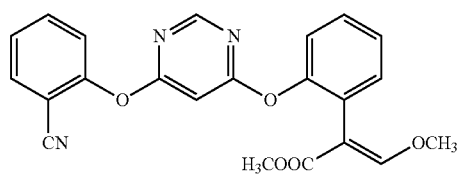
(Ia)

The process of converting compound of formula (VIa) to a compound of formula (Ia) comprises compounds of Formula (VIa) with compounds of Formula (IVa) in presence of 1,5,7-triazabicyclo[4.4.0]dec-5-ene or salts thereof, or derivatives thereof as a catalyst.

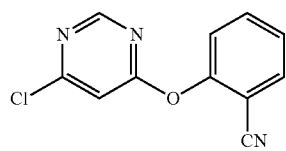
(VIa)

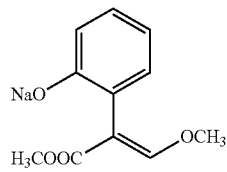
(IVa)

In another embodiment the compound of Formula (Ib) is prepared using the compound of Formula (VIb) and (IVc) in presence of 1,5,7-triazabicyclo[4.4.0]dec-5-ene, salts thereof, or derivatives thereof as a catalyst.

In an embodiment, the process for preparation of a compound of Formula (Ib) comprises (a) reacting a compound of formula (Vb) with a compound of formula (IIIb) in presence of 1,5,7-triazabicyclo[4.4.0]dec-5-ene or salts thereof, or derivatives thereof as a catalyst to get compound of formula (VIb) and

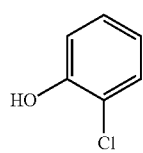
(IIIb)

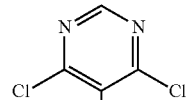
(Vb)

(VIb)

(b) converting compound of formula (VIb) to a compound of formula (Ib).

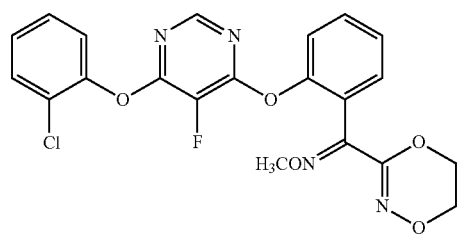
(Ib)

The process of converting compound of formula (VIb) to a compound of formula (Ib) comprises reacting compounds of Formula (VIb) with compounds of Formula (IVc) in presence of 1,5,7-triazabicyclo[4.4.0]dec-5-ene or salts thereof, or derivatives thereof as a catalyst.

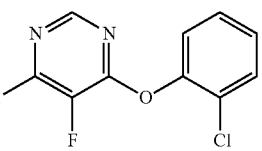
(VIb)

(IVc)

Typically, the process for preparation of fluoxastrobin (Ib) comprises two steps,
1) process for preparing the compound of formula (VIb) and
2) converting the compound of formula (VIb) to compound of formula (Ib).

In one preferred embodiment, the process for preparation of compound of formula (Ib) comprises
a) treating 4,6-Dichloro-5-fluoropyrimidine with chlorophenol in presence of catalytic amount of 1,5,7-triazabicyclo[4.4.0]dec-5-ene or salts thereof, or derivatives thereof to obtain compound (VIb);

b) optionally isolating the pure compound (VIb); and c) converting the compound (VIb) to (E)-2-(2-{[6-(2-chlorophenoxy)-5-fluoro-4-pyrimidinyl]oxy}phenyl)-(5,6-dihydro-1,4,2-dioxazin-3-yl)methanone O-methyl oxime.

In another preferred embodiment, the process for preparation of compound of formula (Ib) comprises a) treating 4,6-Dichloro-5-fluoropyrimidine with chlorophenol in presence of catalytic amount of 1,5,7-triazabicyclo[4.4.0]dec-5-ene or salts thereof or derivatives thereof to obtain compound 4-chloro-6-(2-chlorophenoxy)-5-fluoropyrimidine (VIb);

b) optionally isolating the pure compound (VIb);

c) treating compound of formula (VIb) with (E)-(5,6-dihydro-1,4,2-dioxazin-3-yl)(2-hydroxyphenyl)methanone O-methyl oxime (IVc) in presence of catalytic amount of 1,5,7-triazabicyclo[4.4.0]dec-5-ene or salts thereof or derivatives thereof to give (E)-2-(2-{[6-(2-chlorophenoxy)-5-fluoro-4-pyrimidinyl]oxy}phenyl)-(5,6-dihydro-1,4,2-dioxazin-3-yl)methanone O-methyl oxime;

d) optionally isolating the product; and e) optionally purifying the product by crystallisation to obtain pure product.

In one preferred embodiment, the process for preparation of fluoxastrobin (Ib) comprising treating (E)-(5,6-dihydro-1,4,2-dioxazin-3-yl)(2-hydroxyphenyl)methanone O-methyl oxime with 4-chloro-6-(2-chlorophenoxy)-5-fluoropyrimidine in presence of catalytic amount of 1,5,7-triazabicyclo[4.4.0]dec-5-ene or salts thereof or derivatives thereof and in suitable solvent to give (E)-2-(2-{[6-(2-chlorophenoxy)-5-fluoro-4-pyrimidinyl]oxy}phenyl)-(5,6-dihydro-1,4,2-dioxazin-3-yl)methanone O-methyl oxime (fluoxastrobin).

Preferably, the process for preparation of fluoxastrobin comprises heating a mixture of (E)-(5,6-dihydro-1,4,2-dioxazin-3-yl)(2-hydroxyphenyl)methanone O-methyl oxime, potassium carbonate and catalytic amount of 1,5,7-triazabicyclo[4.4.0]dec-5-ene in a suitable solvent for example methyl isobutyl ketone. The mixture is heated at suitable temperature at about 50-75° C. A solution of 4-chloro-6-(2-chlorophenoxy)-5-fluoropyrimidine in suitable solvent for example methyl isobutyl ketone is added to the above mixture. The reaction is carried out at temperature of about 75-80° C.

The product obtained is (E)-2-(2-{[6-(2-chlorophenoxy)-5-fluoro-4-pyrimidinyl]oxy}phenyl)-(5,6-dihydro-1,4,2-dioxazin-3-yl)methanone O-methyloxime (Ib).

The product thus obtained can be crystallised using suitable solvent for example alcohol to get pure product.

Accordingly there is provided a compound of Formula (Ib) prepared by a process which proceeds via the intermediate compounds of Formula (V1b) prepared in the presence of 1,5,7-triazabicyclo[4.4.0]dec-5-ene or salts thereof, or derivatives thereof as a catalyst.

Fluoxastrobin thus obtained according to the present invention is having high purity of at least 98.7% and reduced dimer impurity content preferably 0.9%.

In another embodiment, the present invention provides a process for the preparation of compounds of Formula (I)

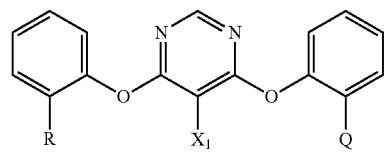

comprising:
reacting compounds of Formula (VI) with compound of Formula (VIIIa) in the presence of a base and 1,5,7-triazabicyclo[4.4.0]dec-5-ene or salts thereof, or derivatives thereof as a catalyst

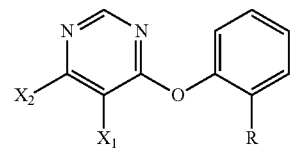

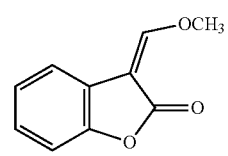

wherein, R is selected from halogen and nitrile;
$X_1$ is selected from hydrogen and halogen, $X_2$ is halogen;
Q is selected from methyl (E)-2-(3-methoxy) acrylate, methyl 2-(3,3-dimethoxy) propanoate, and 5,6-dihydro-1,4,2-dioxazin-3-yl-N-methoxymethanimine In an embodiment the preferred base is sodium methoxide.

In another embodiment the present invention provides a process for the preparation of compounds of Formula (VI)

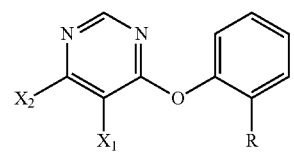

comprising reacting compounds of Formula (V) with compounds of Formula (III)

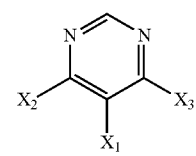

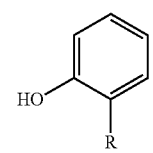

in the presence of 1,5,7-triazabicyclo[4.4.0]dec-5-ene, salts thereof, or derivatives thereof as a catalyst, wherein, R, $X_1$, $X_2$ and $X_3$ has same meaning as defined above.

In an embodiment the process according to the present invention provides a compound of Formula (VI) wherein R is —CN, $X_1$ is hydrogen and $X_2$ is chlorine as represented by Formula (VIa).

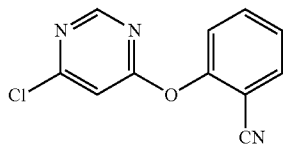

(VIa)

In another embodiment the process according to the present invention provides a compound of Formula (VI) wherein R is chlorine, $X_1$ is fluorine and $X_2$ is chlorine as represented by Formula.

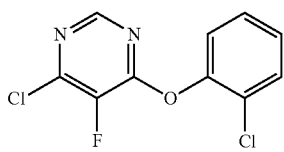

(VIb)

In an embodiment, the process according to the present invention is carried out using a compound of Formula (V) wherein $X_1$ is hydrogen, $X_2$ and $X_3$ are chlorine as represented by Formula (Va).

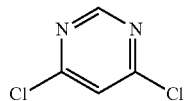

(Va)

In another embodiment, the process according to the present invention is carried out using a compound of Formula (V) wherein $X_1$ is fluorine and $X_2$ and $X_3$ are chlorine as represented by Formula (Vb).

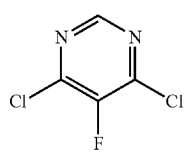

(Vb)

In another embodiment the present invention provides a process for the preparation of compounds of Formula (I)

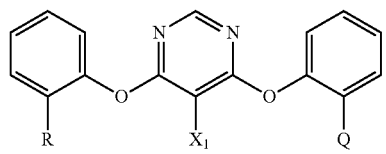

(I)

comprising:
(i) reacting compounds of Formula (V) with compounds of Formula (III) in the presence of 1,5,7-triazabicyclo[4.4.0]dec-5-ene, salts thereof, or derivatives thereof as a catalyst to obtain compounds of Formula (VI); and

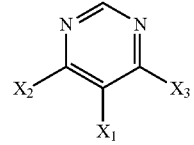

(V)

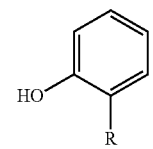

(III)

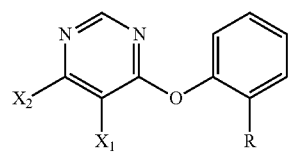

(VI)

(ii) reacting compounds of Formula (VI) with compounds of Formula (IV)

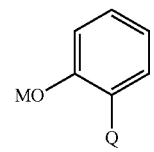

(IV)

in the presence of 1,5,7-triazabicyclo[4.4.0]dec-5-ene, salts thereof, or derivatives thereof as a catalyst to obtain compound of Formula (I) wherein, R is selected from halogen and nitrile, M is hydrogen or an alkali metal, $X_1$, $X_2$, $X_3$ and Q has same meaning as above.

In an embodiment step (i) and step (ii) of the process according to the present invention are carried out in a continuous or stepwise manner.

In another embodiment step (ii) reaction can be carried out with or without isolation of step (i) product.

In an embodiment the processes according to the present invention can be carried out in presence of suitable base selected from inorganic bases such as metal hydroxides, carbonates or bicarbonates, or alkoxides, or organic bases such as aliphatic or aromatic amines. The metal of the inorganic base can be an alkali or alkaline earth metal, for example alkali metals such as lithium, sodium, potassium, etc.; and for example alkaline earth metals such as magnesium, calcium, strontium, barium, etc. In a preferred embodiment the reaction according to the present invention is carried out in presence of carbonates or bicarbonates as a base.

In an embodiment the present invention is carried out in presence of sodium methoxide.

In an embodiment the reaction according to the present invention is carried out in a suitable solvent selected from aliphatic, alicyclic, and aromatic hydrocarbon such as petroleum ether, hexane, heptane, cyclohexane, toluene, xylene, halogenated hydrocarbon such as chloroform, dichloromethane, dichloroethane, chlorobenzene, trichloroethane, esters such as ethyl acetate, methyl acetate, methyl formate, ethyl formate, isopropyl acetate, ethers such as diethyl ether, dimethyl ether, tetrahydrofuran, diisopropylether, methyl-tert-butyl ether, methyl-tert-amyl ether, dioxane, ketones such as acetone, butanone, methyl isobutyl ketone and cyclohexanone, amides such as N,N-dimethylformamide, N,N-dimethylacetamide, N-methylformamide, N-methylpyrrolidone and hexamethylphosphoric triamide, alcohols such as methanol, ethanol, isopropanol and n-propanol.

In a preferred embodiment the reactions according to the present invention is carried out in dimethylformamide.

In another a preferred embodiment the reactions according to the present invention is carried out in methyl isobutyl ketone.

In an embodiment the reactions according to the present invention is carried out at a temperature between 0-150° C.

In an embodiment the reactions according to the present invention is carried out at a temperature between 10-120° C.

In an embodiment the reactions according to the present invention is carried out at a temperature between 50-100° C.

In an embodiment the reactions according to the present invention is carried out at a temperature between 50-80° C.

The processes of the present invention provide highly pure strobilurin compounds of formula (I), specifically azoxystrobin and fluoxastrobin and salts or derivative compounds thereof.

In an embodiment the present invention provides azoxystrobin having a purity of at least about 95%, preferably at least 98%.

In an embodiment the present invention provides fluoxastrobin having a purity of at least about 95% preferably at least 98%.

In an embodiment, the present invention provides a compound of Formula (I) or a compound of Formula (II) having a purity of at least about 95%.

Azoxystrobin prepared according to the any one of the processes described herein is highly pure, particularly having a purity of at least about 95%, preferably at least about 98%.

In an embodiment, the present invention provides a compound of Formula (I) or a compound of Formula (II) having a purity of at least about 97.5%.

It is a known fact that side products and by products of the reaction and adjunct reagents used in the reaction or impurities will, in most of the cases, also be present in the product mixture. Thus, during processing of the product, it must be analyzed for purity, typically, by HPLC, TLC or GC analysis, to determine its purity and suitability for continued processing and, ultimately, for its use. The removal of this impurity requires further separation steps. Therefore, there remains a need for highly pure compound of Formula (I) or a compound of Formula (II) substantially free of the impurities, as well as processes for preparing thereof.

In an embodiment, the term 'impurities' refers to unreacted synthetic intermediates, reagents, solvents, organic and/or inorganic products of side reactions, products of dimerization of intermediates, organic and/or inorganic salts and/or other undesired materials.

The term "substantially free", referred herein mean that the desired compounds contain less than about 1.0 wt % of the impurity, preferably less than about 0.5 wt %, In an embodiment the present invention provides a process for reducing the formation of undesired products/impurity formed during the process of the preparation of strobilurin compounds and/or their intermediates.

The strobilurin compound of Formula (I) produced in high yield and substantially free of impurities according to the present invention.

Typically, the strobilurin compound of Formula (I) prepared according to the present process have purity greater than 95% preferably greater than 98% by HPLC.

Preferably, the processes according to the present invention provide highly pure strobilurin compounds of Formula (I) that are substantially free of impurities; and in particular a dimer impurity below 0.15% by mol.

The processes according to the present process provide intermediates of Formula (II) and Formula (VI) for strobilurin compounds that are substantially free of impurities, in particular, a dimer impurity below 0.15% by mol.

Accordingly, the process according to the present invention provides strobilurin compounds, particularly a compound of Formula (I) or a compound of Formula (II) that is substantially free of certain impurities.

The present inventors observed that in the process of preparation of compound of Formula (I) or a compound of Formula (II) contained about above 0.5% and up to 5% of the dimer impurity represented by a compound of Formula (IX). Advantageously, the content of dimer impurity could be reduced up to 0.15% by using the present process as described herein, and which could be reduced to below 0.15% or eliminated completely.

In an embodiment the present invention provides a compound of Formula (I) or a compound of Formula (II) that is substantially free of an impurity, particularly represented by a compound of Formula (IX).

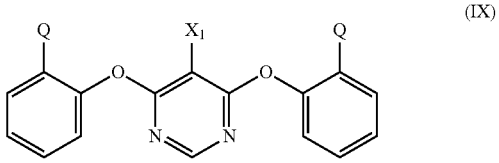

(IX)

wherein $X_1$ is hydrogen and Q is methyl 2-(3,3-dimethoxy)propanoate group and/or methyl (E)-2-(3-methoxy) acrylate group.

In an embodiment the process according to the present invention provides a compound of Formula I or a compound of Formula (II) that is substantially free of an impurity represented by a compound of Formula (IX) wherein $X_1$ is fluorine and Q is (E)-5,6-dihydro-1,4,2-dioxazin-3-yl-N-methoxymethanimine.

In an embodiment the compound of Formula (I) is selected from azoxystrobin. In an embodiment the present invention provides azoxystrobin substantially free from the impurity of Formula (IX).

The strobilurin compounds of Formula (I) or intermediate compound of formula (II) that is substantially free of impurities selected from, a compound of formula (IX) wherein $X_1$ is hydrogen and Q is methyl 2-(3,3-dimethoxy)propanoate group and/or methyl (E)-2-(3-methoxy)acrylate group or a compound of formula (IX) wherein $X_1$ is fluorine and Q is (E)-5,6-dihydro-1,4,2-dioxazin-3-yl-N-methoxymethanimine.

The present process is advantageous in reducing the content of dimer impurity in the strobilurin compounds of Formula (I) or an intermediate compound of formula (VI), preferably the compounds are substantially free of impurities represented by a compound of formula (XI) wherein R is selected from halogen or nitrile and $X_1$ is selected from hydrogen or halogen.

(XI)

In a specific embodiment R is preferably selected from CN, and Cl. In an embodiment the compound of Formula (I) is selected from fluoxastrobin. In an embodiment the present invention provides fluoxastrobin substantially free from the impurity of Formula (XI) preferably less than 1%.

Specifically, the compound of Formula (I) for example azoxystrobin or fluoxastrobin. as disclosed herein, are substantially free from above described dimer impurities. Preferably the content of dimer impurity is reduced to less than about 0.1%, more specifically less than about 0.05%, still more specifically less than about 0.02%, and most specifically essentially free of dimer impurity.

In one embodiment, the process according to the present invention provides strobilurin compounds, particularly a compound of Formula (I) or intermediate compound of Formula (II) that is substantially free of certain impurities, preferably dimer impurity selected from formula (IX) or formula (XI) or their combinations.

Accordingly, the present invention provides highly pure Azoxystrobin having purity at least 98% purity and less than 1% of dimer impurity selected from formula (IX) or formula (XI) or their combinations.

The present invention provides highly pure fluoxastrobin having less than 1% of dimer impurity selected from formula (IX) or formula (XI) or their combinations.

Preferably, Azoxystrobin prepared by a process which proceeds via intermediate compound of formula (II) prepared in presence of 1,5,7-triazabicyclo[4.4.0]dec-5-ene or salts thereof, or derivatives thereof as a catalyst, having purity at least 98% and less than 1% of dimer impurity selected from compound (IX) or compound (XI) or combinations thereof.

Preferably, Fluoxastrobin prepared by a process which proceeds via intermediate compound of formula (II) prepared in presence of 1,5,7-triazabicyclo[4.4.0]dec-5-ene or salts thereof, or derivatives thereof as a catalyst, having purity at least 98% and less than 1% of dimer impurity selected from compound (IX) or compound (XI) or combinations thereof.

The present invention provides Azoxystrobin having purity at least 98% purity and less than 1% of dimer impurity represented by formula (XI) and/or formula (IX).

The present invention provides Fluoxastrobin having purity at least 98% purity and less than 1% of dimer impurity represented by formula (XI) and/or formula (IX).

The present invention further provides azoxystrobin prepared according to the present invention wherein said azoxystrobin is having a volume average particle size distribution D50 up to 300 μm (micrometers). The particles can be further micronized by conventional methods to obtain desired particle size for processing of formulation.

Advantages of the Present Invention are
1. The process is an efficient and commercially viable process.
2. The process provides compounds of Formula (I) and compounds of Formula (II) that is substantially free of certain impurities.
3. The present process advantageously reduced the dimer impurity content in the final products and intermediates preferably about less than 1% of dimer impurity selected from formula (IX) or formula (XI) or their combinations.
4. The invention provides a process for the preparation of strobilurin fungicides in good yield and high purity that are acceptable commercially.

The advantages and other parameters of the present invention is illustrated by the below given examples. However, the scope of the present invention is not limited by the examples in any manner. While the present invention has been described in terms of its specific embodiments, certain modifications and equivalents will be apparent to those skilled in the art and are intended to be included within the scope of the present invention.

EXAMPLES

Example 1

Preparation of (methyl (E)-2-{2-[6-chloropyrimidin-4-yloxy]phenyl}-3-methoxyacrylate (IIa)

4,6-dichloropyrimidine (98%, 92 g, 0.605 moles) was added to a stirred mixture of 3-(methoxy methylene)-2(3H)-benzofuranone (97%, 91 g, 0.5 moles) in methyl formate (275 g) at 10° C. 1,5,7-triazabicyclo[4.4.0]dec-5-ene (0.035 g, 0.25 mmol, 0.05 mole %) was added to the reaction mixture followed by dropwise addition of sodium methoxide (30% in methanol, 110 g, 0.61 moles) at 10 to 15° C. After the addition, the reaction mass was stirred at 10 to 15° C. for 1 hour. Methyl formate was then distilled off while maintaining the temperature below 55° C. Toluene (300 ml) and water (200 ml) were added to the residue and the mixture was stirred at 60-65° C. The mixture was cooled to room temperature and the organic layer was separated. Solvent was distilled off from the reaction mixture under reduced pressure and the oily residue was heated to 130-135° C. Potassium hydrogen sulphate (1.36 g, 0.01 moles) was added and the reaction mixture was stirred at 130-135° C. under 15-22 mm Hg vacuum for 3 hours. The reaction mixture was cooled to room temperature, diluted with toluene (200 ml) and the solution was washed with water. The separated organic layer was distilled off and crude mass was crystallised from methanol (80 ml) to obtain methyl (2E)-2-{2-[(6-chloropyrimidin-4-yl)oxy]phenyl}-3-methoxyacrylate (Purity 97.5%, dimer content 0.98%).

Example 2 (Comparative Example)

Preparation of methyl (E)-2-{2-[6-chloropyrimidin-4-yloxy]phenyl}-3-methoxyacrylate (IIa) in the absence of catalyst To a stirred mixture of 3-(methoxy methylene)-2(3H)-benzofuranone (97%, 91 g, 0.5 moles) in methyl formate (275 g) was added 4,6-dichloropyrimidine (98%, 92 g, 0.605 moles) at 10° C. To the reaction mixture sodium methoxide (30% in methanol 110 g, 0.61 moles) was added dropwise at 10 to 15° C. After the addition, the reaction mass was maintained at 10 to 15° C. for 1 hour. Methyl formate was distilled at atmospheric pressure while maintaining the temperature below 55° C. To the residue was added toluene (300 ml) and water (200 ml) and the mixture was heated at 60-65° C. The mixture was cooled to room temperature and the organic layer was separated. Toluene was distilled off under reduced pressure and the oily residue was heated at 130-135° C. to remove the solvent. Potassium hydrogen sulphate (1.36 g, 0.01 moles) was added and the reaction mixture was stirred at 130-135° C. under 15-22 mm Hg vacuum for 3 h. The reaction mixture was cooled to room temperature and diluted with toluene (200 ml). The toluene solution was washed with water and organic layer was separated. Toluene was distilled off and crude mass crystallised from methanol (80 ml) to obtain methyl (2E)-2-{2-[(6-chloropyrimidin-4-yl)oxy]phenyl}-3-methoxyacrylate (Purity: 73.5%, dimer content: 2.9%)

Example 3

Preparation of Azoxystrobin (Ia)

To a stirred mixture of methyl (E)-2-{2-[6-chloropyrimidin-4-yloxy]phenyl}-3-methoxyacrylate (83.5 g, 0.25 moles), potassium carbonate (52.8 g, 0.375 moles), 2-cyanophenol (33.8 g, 0.275 moles) in DMF (170 g) was added 1,5,7-triazabicyclo[4.4.0]dec-5-ene (0.695 g, 0.005 moles, 2.0 mole %) in DMF (10 ml) at room temperature. The mixture was heated to 90° C. and stirred at same temperature for 7-8 hours. The reaction mixture was cooled to 50-55° C. and filtered to remove the salt. DMF was distilled at 70-80° C. under vacuum. The residual mass was crystalized from a mixture of methanol (90 ml) and water (10 ml) to obtain the product (Purity: 98%, dimer content: 0.78%).

Example 4 (Comparative Example)

The Preparation of Azoxystrobin (Compound of Formula Ia) in the Absence of Catalyst To a stirred mixture of methyl (E)-2-{2-[6-chloropyrimidin-4-yloxy]phenyl}-3-methoxyacrylate (83.5 g, 0.25 moles), potassium carbonate (52.8 g, 0.375 moles), 2-cyanophenol (33.8 g, 0.275 moles) in DMF (170 g) was added at room temperature. The mixture was heated to 90° C. and stirred at same temperature for 10-12 hrs. The reaction mixture was cooled to 50-55° C. and filtered to remove the salt. The filtrate was distilled to recover DMF at 70-80° C. under vacuum. The residual mass was crystalized from a mixture of methanol (90 ml) and water (10 ml) to obtain product. (Purity: 76.4%, dimer content: 2.5%).

Example 5

The Preparation of Azoxystrobin (Ia)

To a stirred mixture of methyl (E)-2-{2-[6-chloropyrimidin-4-yloxy]phenyl}-3-methoxyacrylate (83.5 g, 0.25 moles), potassium carbonate (52.8 g, 0.375 moles), 2-cyanophenol (33.8 g, 0.275 moles) in DMF (170 g) was added 1,5,7-triazabicyclo[4.4.0]dec-5-ene (0.348 g, 0.0025 moles, 1.0 mole %) in DMF (10 ml) at room temperature. The mixture was heated to 90° C. and stirred at same temperature for 7-8 hours. The reaction mixture was cooled to 50-55° C. and filtered to remove the salt. The filtrate was distilled to recover DMF at 70-80° C. under vacuum. The residual mass was crystalized from a mixture of methanol (90 ml) and water (10 ml) to obtain the product (Purity: 98.4%, dimer content: 0.34%).

Example 6

The Preparation of Azoxystrobin (Ia)

To a stirred mixture of methyl (E)-2-{2-[6-chloropyrimidin-4-yloxy]phenyl}-3-methoxyacrylate (83.5 g, 0.25 moles), potassium carbonate (52.8 g, 0.375 moles), 2-cyanophenol (33.8 g, 0.275 moles) in DMF (170 g) was added 1,5,7-triazabicyclo[4.4.0]dec-5-ene (0.00348 g, 0.025 mmoles, 0.01 mole %) in DMF (10 ml) at room temperature. The mixture was heated to 90° C. and stirred at same temperature for 7-8 hours. The reaction mixture was cooled to 50-55° C. and filtered to remove the salt. The filtrate was distilled to recover DMF at 70-80° C. under vacuum. The residual mass was crystalized from a mixture of methanol (90 ml) and water (10 ml) to obtain the product (purity: 98.2%, dimer content: 0.77%).

Example 7

Preparation of Azoxystrobin (Ia)

To a stirred mixture of methyl (E)-2-{2-[6-chloropyrimidin-4-yloxy]phenyl}-3-methoxyacrylate (83.5 g, 0.25 moles), potassium carbonate (52.8 g, 0.375 moles), 2-cyanophenol (33.8 g, 0.275 moles) in DMF (170 g) was added 1,5,7-triazabicyclo[4.4.0]dec-5-ene (0.173 g, 0.001 moles, 0.5 mole %) in DMF (10 ml) at room temperature. The mixture was heated to 90° C. and stirred at same temperature for 7-8 hours. The reaction mixture was cooled to 50-55° C. and filtered to remove the salt. The filtrate was distilled to recover DMF at 70-80° C. under vacuum. The residual mass was crystalized from a mixture of methanol (90 ml) and water (10 ml) to obtain the product. (Purity: 98.6%, dimer content: 0.3%).

Example 8

Preparation of 2-[(6-chloro-4-pyrimidinyl)oxy]-benzonitrile (Compound VIa)

4,6-Dichloropyrimidine (98%, 92 g, 0.605 moles), potassium carbonate (104.5 g, 0.756 moles), 1,5,7-triazabicyclo[4.4.0]dec-5-ene (0.042 g, 0.3 mmol, 0.05 mole %) were stirred in methyl isobutyl ketone (240 ml) at 60 to 65° C., To this mixture was dropwise o-cyanophenol (72.66 g, 0.61 moles) in of methyl isobutyl ketone (200 ml). The mixture was stirred at 60° C. for 6 hours and then cooled, the organic phase was separated and washed with 5% NaOH, the aqueous phase was extracted with methyl isobutyl ketone, the organic extracts were combined and dried over sodium sulphate, the solvent was partially distilled. The product was crystallised, filtered and dried to get 2-[(6-chloro-4-pyrimidinyl)oxy]-benzonitrile (Purity: 98%, dimer: 0.55%).

Example 9

Preparation of Azoxystrobin (Ia)

To a stirred mixture of 3-(methoxy methylene)-2(3H)-benzofuranone (97%, 181.4 g, 1.0 moles) in methyl formate (566 g) was added 2-[(6-chloro-4-pyrimidinyl)oxy]-benzonitrile (96.6%, 251.7 g, 1.05 moles) at 10-15° C. To the reaction mixture was added 1,5,7-triazabicyclo[4.4.0]dec-5-ene (2.86 g, 0.02 moles, 2.0 mole %) followed by dropwise addition of sodium methoxide (30% in methanol, 219.6 g, 1.22 moles) at 10 to 15° C. After addition is over, the reaction mass was maintained at 10 to 15° C. for 1 hour. Methyl formate was then distilled off while maintaining the temperature between 55-65° C. To the residue was added toluene (700 ml) and water (400 ml) and the mixture was heated to 65-70° C. and stirred for 1 hour. The mixture was cooled to room temperature and the organic layer was separated. Toluene was distilled off under reduced pressure and the oily residue was heated to 78-80° C. To this residue acetic anhydride was dropwise added at 78-80° C. and the mixture was cooked for 30 minutes. To the mixture, methane sulphonic acid (8 g) was added dropwise and mixture was stirred for 3 hours. After completion of reaction was diluted with water (250 ml) and the mixture was heated to 65-70° C. for 30 minutes. The organic layer was washed with 10% sodium bicarbonate (200 ml). The organic layer was separated, dried and concentrated at reduced pressure. The residual mass was crystallised from methanol (450 ml) to obtain the product. (Purity: 98.9%, dimer content: 0.23%).

Example 10

The Preparation of 4-chloro-6-(2-chlorophenoxy)-5-fluoropyrimidine (VIb)

4,6-Dichloro-5-fluoropyrimidine (98%, 92 g, 0.539 moles), potassium carbonate (93.30 g, 0.675 moles), 1,5,7-triazabicyclo[4.4.0]dec-5-ene (0.751 g, 0.0054 mmol, 1.0 mole %) were stirred in methyl isobutyl ketone (240 ml) at 60 to 65° C. To this mixture, 2-chlorophenol (72.72 g, 0.565 moles) in methyl isobutyl ketone (200 ml) was added dropwise. The mixture was heated to 70° C. and stirred for 10 hours and then cooled, the organic phase was separated and washed with 5% NaOH, the aqueous phase was extracted with methyl isobutyl ketone, the organic extracts were combined and dried over sodium sulphate and the solvent was distilled to get 4-chloro-6-(2-chlorophenoxy)-5-fluoropyrimidine. (Purity: 98.1%, dimer: 0.91%).

Example 11

The Preparation of Fluoxastrobin (Ib)

A mixture of (E)-5,6-dihydro-1,4,2-dioxazin-3-yl-(2-hydroxyphenyl)methanone-O-methyloxime (236.079 g, 1 mole), potassium carbonate (172.75 g), 1,5,7-triazabicyclo[4.4.0]dec-5-ene (7 g, 0.046 moles, 5 mole %), in methyl isobutyl ketone (800 ml) and water (400 ml) was heated to 60° C. A solution of 4-chloro-6-(2-chlorophenoxy)-5-fluoropyrimidine (267 g, 1 mole) in methyl isobutyl ketone (200 ml) was added to the mixture at the same temperature under stirring. The reaction mixture is then heated to 75-80° C. and stirred for 8 hours. The reaction mixture is cooled to room temperature and water (800 ml) is added, the organic layer is separated, and the aqueous layer is extracted with methyl isobutyl ketone (100 ml), the combined organic layers are dried over sodium sulphate and the solvent is distilled off. The product was crystallised from methanol to give (E)-2-(2-{[6-(2-chlorophenoxy)-5-fluoro-4-pyrimidinyl]oxy}phenyl)-(5,6-dihydro-1,4,2-dioxazin-3-yl)methanone O-methyloxime (Purity: 98.5%, dimer content: 0.53%).

Example 12

The Preparation of Fluoxastrobin (Ib)

A mixture of (E)-5,6-dihydro-1,4,2-dioxazin-3-yl-(2-hydroxyphenyl)methanone-O-methyloxime (105 g, 0.44 moles), potassium carbonate (82 g, 0.59 moles) and 1,5,7-triazabicyclo[4.4.0]dec-5-ene (1.3 g, 0.01 moles, 2.0 mole %) in methyl isobutyl ketone (400 ml) and water (100 ml) was heated to 60° C.. A solution of 4-chloro-6-(2-chlorophenoxy)-5-fluoropyrimidine (120 g, 044 moles) in methyl isobutyl ketone (100 ml) was added dropwise to the mixture at the same temperature. The resulting reaction mixture was heated to 75-80° C. and stirred for 8 hours. The reaction mixture was cooled to room temperature and quenched with water (400 ml) and the organic layer was separated, and the aqueous layer was extracted with methyl isobutyl ketone (100 ml), the combined organic extracts were dried over sodium sulphate and the solvent was distilled. The product was crystallised in methanol to give (E)-2-(2-{[6-(2-chlorophenoxy)-5-fluoro-4-pyrimidinyl]oxy}phenyl)-(5,6-dihydro-1,4,2-dioxazin-3-yl)methanone O-methyloxime. (Purity: 98.7%, dimer content: 0.65%)

Example 13 (Comparative Example)

The Preparation of Fluoxastrobin (Ib)

A mixture of (E)-5,6-dihydro-1,4,2-dioxazin-3-yl-(2-hydroxyphenyl)methanone-O-methyloxime (105 g, 0.44 moles), potassium carbonate (82 g, 0.59 moles) in methyl isobutyl ketone (400 ml) and water (100 ml) was heated to 60° C. A solution of 4-chloro-6-(2-chlorophenoxy)-5-fluoropyrimidine (120 g, 044 moles) in methyl isobutyl ketone (100 ml) was added dropwise to the mixture at the same temperature. The resulting reaction mixture was heated to 75-80° C. and stirred for 8 hours. The reaction mixture was cooled to room temperature and quenched with water (400 ml) and the organic layer was separated, and the aqueous layer was extracted with methyl isobutyl ketone (100 ml), the combined organic extracts were dried over sodium sulphate and the solvent was distilled. The product was crystallised in methanol to give (E)-2-(2-{[6-(2-chlorophenoxy)-5-fluoro-4-pyrimidinyl]oxy}phenyl)-(5,6-dihydro-1,4,2-dioxazin-3-yl)methanone O-methyloxime. (Purity: 71.2%, dimer content: 3.5%).

We claim:
1. A process for preparation of a compound of Formula (I) comprising:

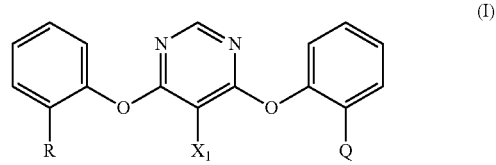

reacting a compound of Formula (II) with a compound of Formula (III) in the presence of a 1,5,7-triazabicyclo[4.4.0]dec-5-ene or a salt thereof as a catalyst;

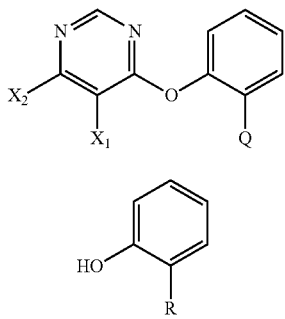

(II)

(III)

wherein,
R is selected from halogen and nitrile;
$X_1$ is selected from hydrogen and fluorine;
$X_2$ is chlorine; and
Q is selected from methyl (E)-2-(3-methoxy) acrylate, methyl 2-(3,3-dimethoxy) propanoate, and 5,6-dihydro-1,4,2-dioxazin-3-yl-N-methoxymethanimine.

2. The process according to claim 1, wherein the 1,5,7-triazabicyclo[4.4.0]dec-5-ene or salt thereof is selected from group consisting of a compound of Formula (VII), (VIIa), (VIIb) and (VIIc), wherein $R_1$ is selected from hydrogen, hydroxyl, $C_1$-$C_{20}$ hydrocarbonyl, amino, $C_1$-$C_6$ alkyl amino, cyano and halogen

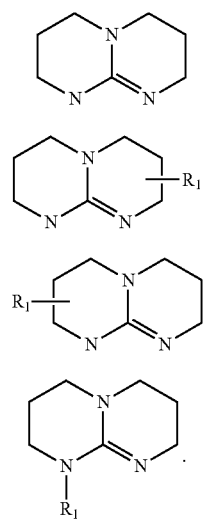

(VII)

(VIIa)

(VIIb)

(VIIc)

3. The process according to claim 1, wherein said catalyst is used in an amount of about 0.01 mol % to about 50 mol %.

4. A process for preparation of a compound of Formula (II) comprising:

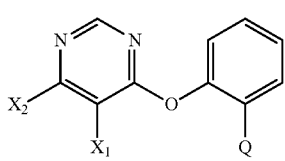

(II)

reacting a compound of Formula (V) with a compound of Formula (IV) in the presence of a 1,5,7-triazabicyclo[4.4.0]dec-5-ene or a salt thereof as a catalyst;

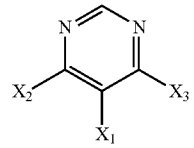

(V)

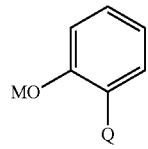

(IV)

wherein,
$X_1$, $X_2$ and $X_3$ are independently selected from hydrogen, chlorine and fluorine;
M is selected from hydrogen and an alkali metal; and
Q is selected from methyl (E)-2-(3-methoxy) acrylate, methyl 2-(3,3-dimethoxy) propanoate, and 5,6-dihydro-1,4,2-dioxazin-3-yl-N-methoxymethanimine.

5. The process as claimed in claim 4, wherein said compound of formula (II) is at least one compound selected from

(IIa)

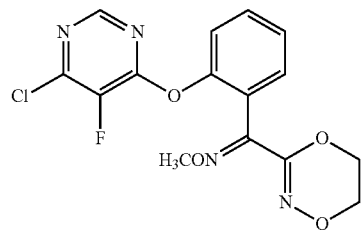

(IIc)

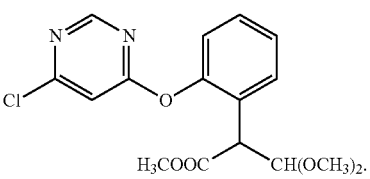

(IIb)

6. The process as claimed in claim 1, wherein said process is carried out at a temperature in the range of about 0-150° C. for 2 to 30 hrs.

7. A process for preparation of a compound of Formula (I) comprising:

(I)

reacting a compound of Formula (VI) with a compound of Formula (IV) in the presence of a 1,5,7-triazabicyclo[4.4.0]dec-5-ene or a salt thereof as a catalyst (VI)

(IV)

wherein R is selected from halogen and nitrile; $X_1$ is selected from hydrogen and fluorine, $X_2$ is selected from chlorine and fluorine; Q is selected from methyl (E)-2-(3-methoxy) acrylate, methyl 2-(3,3-dimethoxy) propanoate, and 5,6-dihydro-1,4,2-dioxazin-3-yl-N-methoxymethanimine; and M is selected from hydrogen and sodium.

8. The process according to claim 7, wherein the 1,5,7-triazabicyclo[4.4.0]dec-5-ene or salt thereof is selected from group consisting of a compound of Formula (VII), (VIIa), (VIIb) and (VIIc), wherein $R_1$ is selected from hydrogen, hydroxyl, $C_1$-$C_{20}$ hydrocarbonyl, amino, $C_1$-$C_6$ alkyl amino, cyano or halogen (VII)

(VIIa)

(VIIb)

(VIIc)

9. The process as claimed in claim 7, wherein said compound of Formula (VI) is selected from (VIa)
and (VIb)

10. The process as claimed in claim 7, wherein said compound of Formula (IV) is selected from the compounds represented by formulas (IVa)

(IVb)

and (IVc)

11. The process as claimed in claim 7, wherein said process is carried out at a temperature in the range of about 0-150° C. for 1 to 24 hrs.

12. The process according to claim 1, wherein said compound of formula (I) is azoxystrobin.

13. The process for preparation of the compound of formula (I) as claimed in claim 1, wherein the compound of formula (I) is azoxystrobin (Ia)

(Ia)

comprising reacting a compound of formula (IV) with a compound of formula (V) in the presence of the 1,5,7-triazabicyclo[4.4.0]dec-5-ene or salt thereof, wherein formula (IV) is (IVa) and formula (V) is (Va), to provide a compound of formula (II), wherein formula (II) is (IIa)

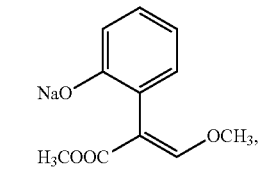
(IVa)

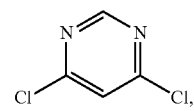
(Va)

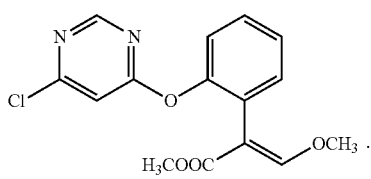
(IIa)

14. The process for preparation of the compound of formula (I) as claimed in claim 1, wherein the compound of formula (I) is azoxystrobin (Ia)

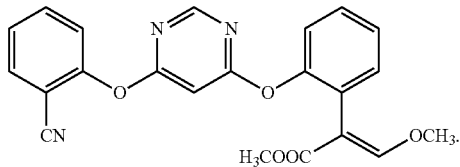
(Ia)

comprising
a) reacting a compound of formula (IV) with a compound of formula (V) in the presence of the 1,5,7-triazabicyclo[4.4.0]dec-5-ene or salt thereof, wherein formula (IV) is (IVb) and formula (V) is (Va), to provide a compound of formula (IIb) and

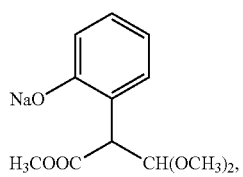
(IVb)

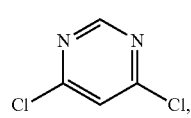
(Va)

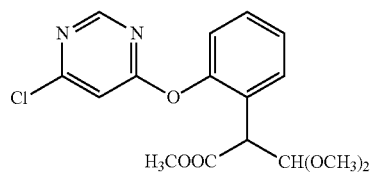
(IIb)

b) reacting the compound of formula (II) with the compound of formula (III) in the presence of the 1,5,7-triazabicyclo[4.4.0]dec-5-ene or salt thereof, wherein formula (II) is formula (IIb) and formula (III) is formula (IIIb), to form the compound of formula (Ia)

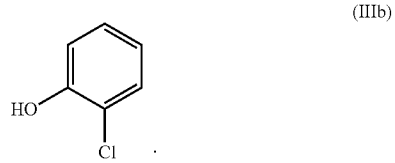
(IIIb)

15. The process according to claim 1, wherein said compound of formula (I) is fluoxastrobin.

16. The process of claim 1 for preparation of fluoxastrobin (Ib) comprising
a) reacting a compound of formula (Vb) with a compound of formula (IIIb) in the presence of the 1,5,7-triazabicyclo[4.4.0]dec-5-ene or salt thereof to provide a compound of formula (VIb) and

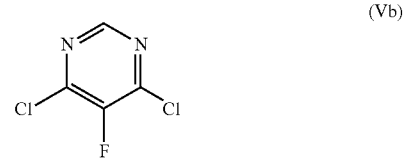
(Vb)

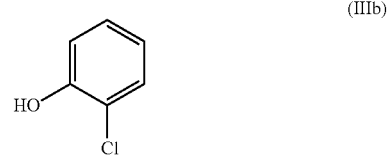
(IIIb)

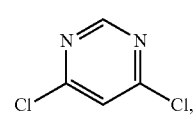
(VIb)

b) reacting the compound of formula (VIb) with a compound of Formula (IVc) in the presence of the 1,5,7-triazabicyclo[4.4.0]dec-5-ene or salt thereof to form the compound of formula (Ib)

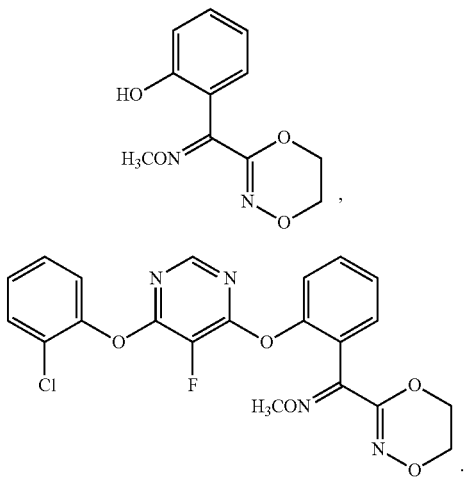
(IVc)

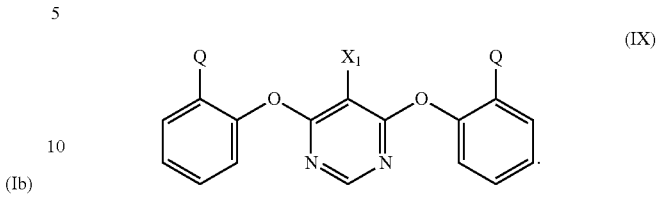

or by a compound of formula (IX) wherein $X_1$ is fluorine and Q is (E)-5,6-dihydro-1,4,2-dioxazin-3-yl-N-methoxymethanimine (Ib)

17. The process of claim 4, wherein said catalyst is used in an amount of about 0.01 mol % to about 50 mol %.

18. The process as claimed in claim 1, wherein the process provides a strobilurin compound of Formula (I) having a purity at least 98% that is substantially free of impurities represented by a compound of formula (IX) wherein $X_1$ is hydrogen and Q is methyl 2-(3,3-dimethoxy)propanoate group and/or methyl (E)-2-(3-methoxy)acrylate group and/

19. The process as claimed in claim 1, wherein the process provides a strobilurin compound of Formula (I) having a purity of at least 98% that is substantially free of impurities represented by a compound of formula (XI) wherein $X_1$ is selected from hydrogen or fluorine and R is selected from nitrile or halogen

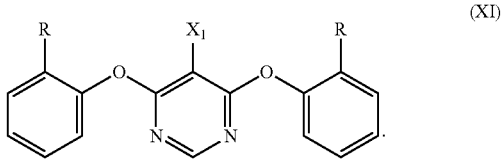
(XI)

\* \* \* \* \*